United States Patent

Ali et al.

[11] Patent Number: 5,799,674
[45] Date of Patent: Sep. 1, 1998

[54] DENTAL FLOSSING DEVICE

[76] Inventors: Sayel A. Ali, 1501 37th Ave. South, Fargo, N. Dak. 58104; Kassab Al-Mahareeq; Hasan Al-Mahrouq, both of 2301 S. Beulah Ave., Indianapolis, Ind. 46241

[21] Appl. No.: 582,589

[22] Filed: Jan. 3, 1996

[51] Int. Cl.$^6$ .................................................. A61C 15/04
[52] U.S. Cl. ........................................... 132/324; 132/322
[58] Field of Search .................................. 132/323, 324, 132/325, 326, 327; 433/140, 93, 322

[56] References Cited

U.S. PATENT DOCUMENTS

| | | | |
|---|---|---|---|
| 924,543 | 6/1909 | Dysart | 132/324 |
| 2,823,455 | 2/1958 | Sprague | 433/93 |
| 2,872,930 | 2/1959 | Patterson | 132/323 |
| 3,814,114 | 6/1974 | Roberts | 132/326 |
| 3,886,956 | 6/1975 | Cash | 132/326 |
| 3,998,236 | 12/1976 | Koo | 132/324 |
| 4,253,477 | 3/1981 | Eichman | 132/323 |
| 4,307,740 | 12/1981 | Florindez et al. | 132/322 |
| 4,522,216 | 6/1985 | Bunker | 132/92 |
| 4,556,074 | 12/1985 | Morin et al. | 132/92 |
| 4,660,584 | 4/1987 | Wofford | 132/92 A |
| 4,807,651 | 2/1989 | Naydich | 132/323 |
| 4,830,032 | 5/1989 | Jousson | 132/323 |
| 4,920,992 | 5/1990 | Preciutti | 132/323 |
| 4,936,326 | 6/1990 | Eckroat | 132/326 |
| 4,995,361 | 2/1991 | Lorenzana et al. | 132/324 |
| 5,010,906 | 4/1991 | Preciutti | 132/323 |
| 5,016,660 | 5/1991 | Boggs | 132/322 |
| 5,020,554 | 6/1991 | Feinberg | 132/323 |
| 5,029,593 | 7/1991 | Huttunen | 132/323 |
| 5,038,806 | 8/1991 | Ewald | 132/325 |
| 5,056,540 | 10/1991 | Page | 132/323 |
| 5,060,681 | 10/1991 | Westbrook et al. | 132/325 |
| 5,069,233 | 12/1991 | Ritter | 132/322 |
| 5,094,256 | 3/1992 | Barth | 132/322 |
| 5,123,432 | 6/1992 | Wyss | 132/323 |
| 5,170,809 | 12/1992 | Imai et al. | 132/322 |
| 5,184,632 | 2/1993 | Gross et al. | 132/326 |
| 5,197,498 | 3/1993 | Stewart | 132/325 |
| 5,207,773 | 5/1993 | Henderson | 132/322 |
| 5,224,500 | 7/1993 | Stella | 132/322 |
| 5,232,002 | 8/1993 | McClallen | 132/325 |
| 5,261,430 | 11/1993 | Mochel | 132/322 |
| 5,267,579 | 12/1993 | Bushberger | 132/322 |
| 5,280,797 | 1/1994 | Fry | 132/323 |
| 5,287,865 | 2/1994 | Fulton | 132/323 |
| 5,392,795 | 2/1995 | Gathani | 132/323 |
| 5,400,811 | 3/1995 | Melbauer | 132/322 |

FOREIGN PATENT DOCUMENTS 1342182  12/1973  United Kingdom .................. 132/323

*Primary Examiner*—Todd E. Manahan
*Assistant Examiner*—E. Robert
*Attorney, Agent, or Firm*—Ice Miller Donadio & Ryan; Paul B. Overhauser

[57] ABSTRACT

A flossing device having a stabilizing member and preferably a thumb-driven floss movement mechanism. In one embodiment, the flossing device includes a shaft includes an operative end and a distal end, the distal end terminating in first and second fork arms. The fork arms each have a closed end connected to the shaft and an open end, and each include an aperture for receiving dental floss. The flossing device also preferably includes a stabilizing member attached to and between the first and second fork arms, said stabilizing member operable to be engaged by teeth to reduce movement of the shaft when the shaft is inserted into the mouth. The flossing device also preferably includes a thumb-driven floss movement mechanism operably attached to the shaft. This mechanism is operable to cause dental floss to move between the apertures of the first and second fork arms, thereby effectuating cleaning action by the dental floss.

19 Claims, 5 Drawing Sheets

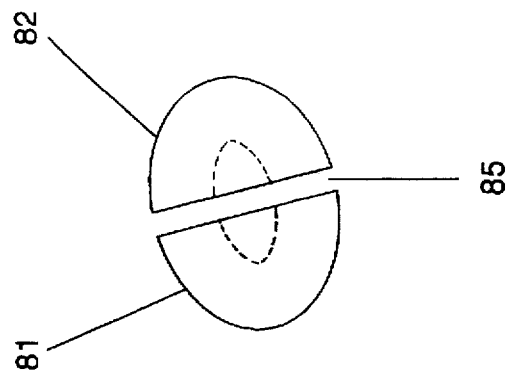
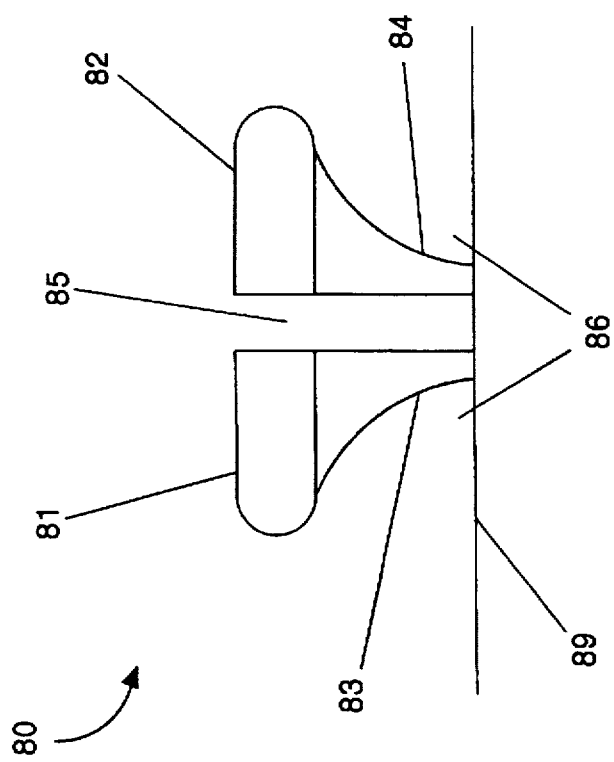

DENTAL FLOSSING DEVICE

FIELD OF THE INVENTION

The present invention relates generally to the field of dental hygiene devices, and in particular, to dental flossing devices.

BACKGROUND OF THE INVENTION

The use of dental floss is considered to be of great importance in the exercise of healthy dental hygiene. Dentists recommend at least daily use of dental floss in conjunction with brushing to promote health teeth and gums. Because of the difficulty and discomfort of flossing the teeth, many flossing devices have been developed in the prior art.

A first class of such prior art devices includes non-motorized flossing stationary flossing devices. For example, the dental cleansing device shown in U.S. Pat. No. 5,094,256 to Barth ("Barth") includes a fork-shaped device having two arms extending from the distal end of a shaft. One end of a length of dental floss is fastened to the shaft. From the shaft, the floss is strung through an aperture in one arm, through an aperture in a second art, and strung down to and fastened to the shaft at the other end. The floss is strung tightly between the two fastening points to provide a tight length of floss between the arms of the device. The user then holds the operative end of the shaft and positions tight length of shaft between abutting teeth. The user causes cleansing action to take place by moving the shaft in a reciprocating manner, which movement is directly translated to the floss.

The drawback of this and similar devices are that only the small length of floss between the arms is available for cleansing at any one time, and gets dirty and worn quickly, requiring constant restringing. Further more, the reciprocating motion of the arms within the mouth can cause the arms to hit and irritate the gums and cheeks.

Another group of fork-shaped devices include a motorized mechanism for causing movement of the dental floss relative to the shaft and thus the teeth. In U.S. Pat. No. 5,184,632 to Gross et al. ("Gross et al."), a length of floss is secured such that it extends tautly between two arms of the device. A motor causes circular motion of the floss to effectuate cleaning action. Another device shown in U.S. Pat. No. 5,224,500 to Stella ("Stella") shows a motor and cam mechanism that causes a length of floss to reciprocate between two arms. The reciprocating floss movement effectuates cleaning when the floss is inserted around or between abutting teeth.

Motorized flossing devices such as the Stella device provide floss movement without requiring the movement of the shaft or arms of the structure. As a result, they provide an advantage over devices such as that described in Barth in that floss motion is achieved without having to effectuate motion of the arms within the mouth. A drawback of the motorized flossing devices is that they are mechanically complex, presenting manufacturing difficulty and reliability questions. A further drawback of such devices is that they require a source of power, such as batteries. Finally, such devices involve the placement of an electrical appliance into the mouth, thereby requiring extra safety mechanisms to be employed.

Another problem inherent with flossing devices is the requirement of steady arm control during use. In the use of flossing devices, only small controlled movements, or in some cases no movement at all, is required. Such control over the flossing device can cause the user to experience hand and arm fatigue. Consequently, a need exists for a flossing device that when used, requires less control and thereby reduces hand and arm fatigue.

SUMMARY OF THE INVENTION

It is an object of the present invention to provide an easy to use flossing device that reduces arm and hand fatigue in use.

It is a further object of the invention to provide a flossing device that effectuates cleaning action using reciprocal motion of the floss with respect to the arms of the device.

It is yet a further object of the invention to provide a flossing device that uses reciprocal motion of the floss to effectuate cleaning without requiring a source of electrical power.

It is yet a further object of the invention to provide a flossing device that is easy to position within the oral cavity.

It is yet a further object of the present invention to provide an easy to use flossing device that is relatively simple to manufacture.

These and other objects of the present invention may be accomplished by a flossing device having a stabilizing member and a thumb-driven floss movement mechanism according to the present invention.

In a preferred embodiment, the flossing device includes a shaft having an operative end and a distal end, said distal end terminating in first and second fork arms. The fork arms each have a closed end connected to the shaft and an open end, and each include an aperture for receiving dental floss. The flossing device also includes a stabilizing member attached to and between said first and second fork arms, said stabilizing member operable to be engaged by teeth to reduce movement of the shaft when the shaft is inserted into the mouth. The flossing device also preferably includes a thumb-driven floss movement mechanism operably attached to the shaft. This mechanism is operable to cause dental floss to move between the apertures of the first and second fork arms, thereby effectuating cleaning action by the dental floss.

The above described features and advantages, as well as other features and advantages, will become readily apparent to those of ordinary skill in the art by reference to the following detailed description and accompanying drawings.

BRIEF DESCRIPTION OF THE DRAWINGS

FIG. 5a shows a side-view cross section of a floss post for use in connection with a flossing device according to the present invention; and FIG. 5b shows a top view of the floss post of FIG. 5a.

DETAILED DESCRIPTION

Figure 1:
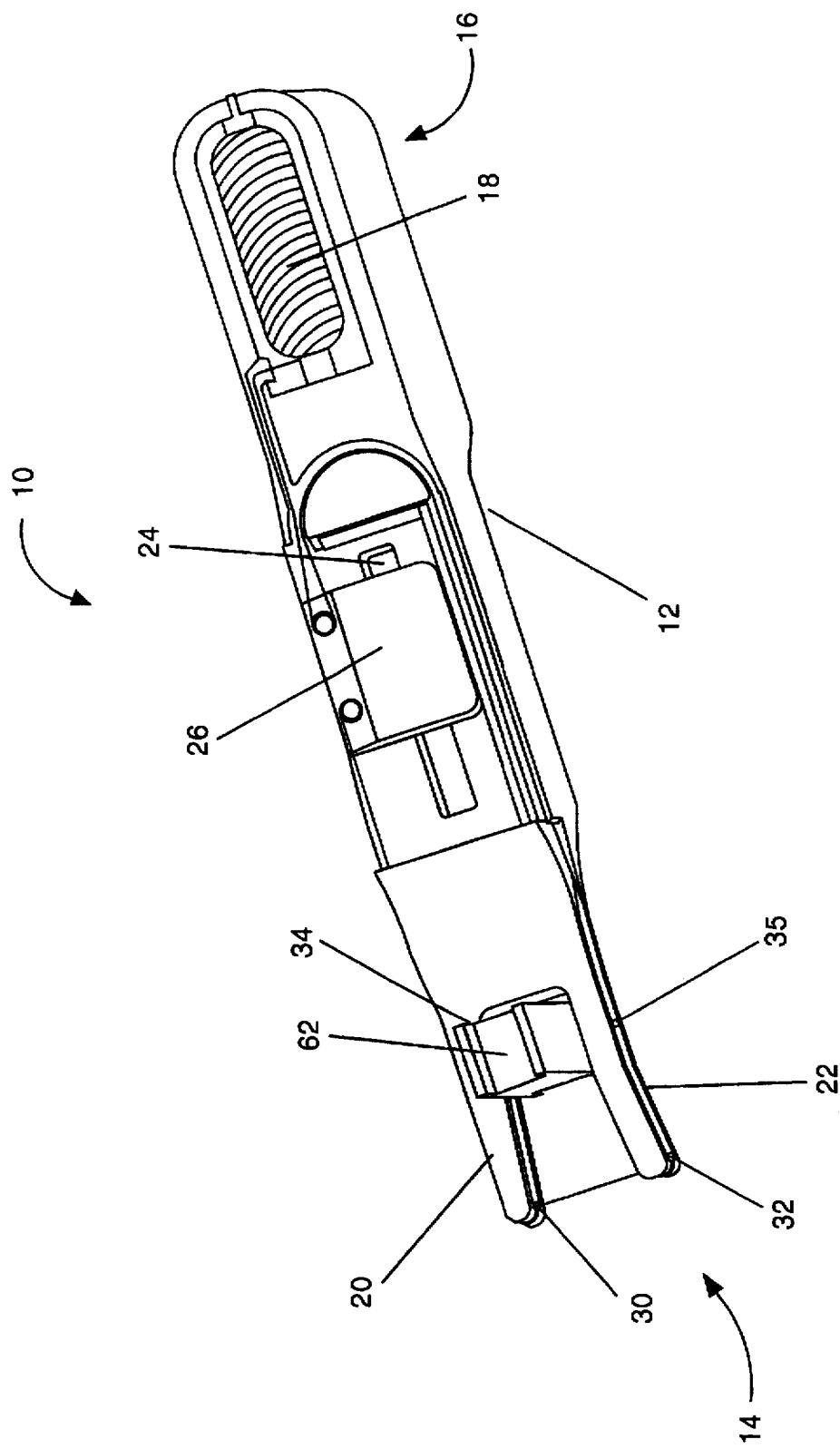
FIG. 1 shows a perspective view of a flossing device according to the present invention.

FIG. 1 shows a perspective view of a flossing device 10 according to the present invention. The flossing device 10 comprises a shaft 12 having a distal end 14 and an operative end 16. The shaft 12 includes a floss chamber 18 proximate to the operative end 16 and first and second fork arms 20 and 22 located at the distal end 14. The shaft 12 and fork arms 20 and 22 are preferably composed of plastic material.

The fork arms 20 and 22 each have a closed end that connects to the rest of the shaft 12 and an open end. The first and second fork arms 20 and 22 respectively taper outward with respect to each other from closed end to their widest distance apart at the open end. The fork arms 20 and 22 are preferably flexible and allow temporary plastic deformation when force is exerted on them. An aperture 30 extends through the first arm 20 and an aperture 32 extends through the second arm 22. The apertures 30 and 32 are located proximate to the open end of the arms 20 and 22 and are generally aligned with respect to each other to allow a length of dental floss to extend therethrough.

A stabilizing member 34 rotatably connected to the first and second arms 20 and 22 such that at least partial rotational motion is possible about an axis defined by a line extending through the first and second arms 20 and 22. The stabilizing member 34 rotates about a pin 35 that is attached to both the first and second arms 20 and 22. The stabilizing member 34 generally extends through the opening defined by the interior of the fork arms 20 and 22 and includes at least one tooth receiving surface 62.

Figure 2:
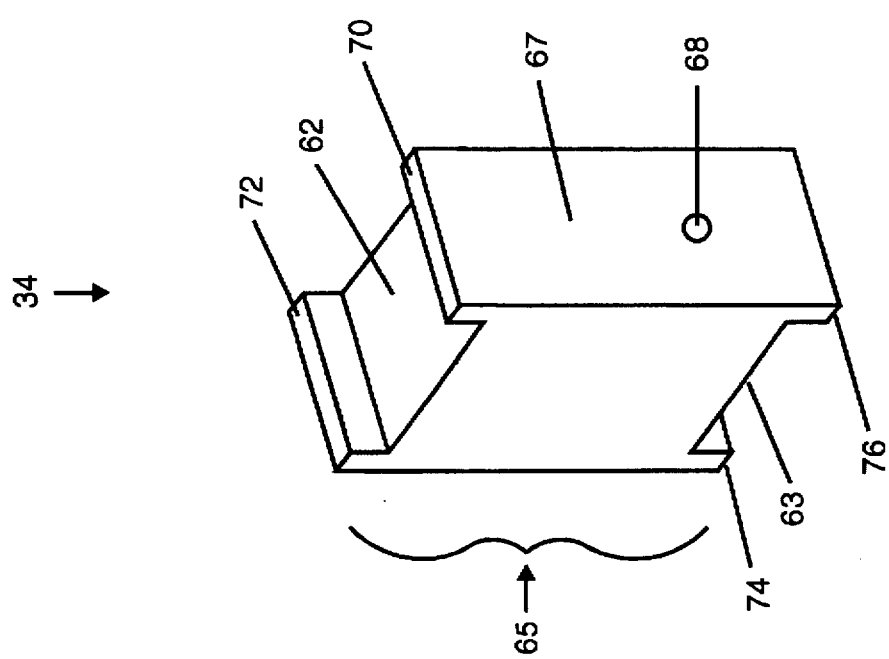
FIG. 2 shows a stabilizing member which may be employed in a flossing device such as the flossing device shown in FIG. 1.

FIG. 2 illustrates in further detail the stabilizing member 34 that is employed in the flossing device 10 of FIG. 1. While the stabilizing member 34 is designed to be utilized in conjunction with the flossing device 10, a similar stabilizing member may be employed in other flossing devices having a forked shaft to produce beneficial results.

The stabilizing member 34 has a top tooth receiving surface 62 and a bottom tooth receiving surface 63 which are spaced apart by a member body 65. The member body 65 includes a first side 67 and an identical and oppositely situated second side, not shown. A tubal opening 68 extends from the first side 67 to the second side and is formed to receive a pin or axle, not shown, such that the stabilizing member 34 can rotate around the pin or axle. The top tooth receiving surface preferably includes raised retaining ridges 70 and 72, one ridge 70 extending along an edge defined by the intersection of the first side 67 and the top tooth receiving surface 62 and another ridge 72 extending along an edge defined by the intersection of the second side and the top tooth receiving surface 62. The bottom tooth receiving surface 63 preferably includes analogously located raised retaining ridges 74 and 76.

Referring again to FIG. 1, an elongated linear channel 24 within the shaft 12 extends between the floss chamber 18 and the fork arms 20 and 22. A sliding member 26 is slidable engaged with the channel 24 to allow linear movement of the sliding member 26 along the dimensions of the channel 24. The sliding member 26 is shown in further detail in FIG. 3.

Figure 3:
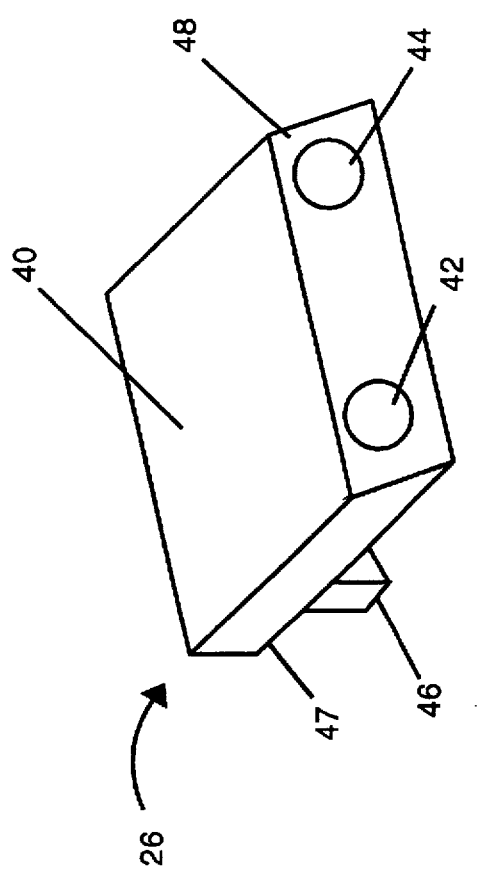
FIG. 3 shows a sliding member for use in flossing device shown in FIGS. 1.

Referring to FIG. 3, the sliding member 26 includes a thumb engagement surface 40, first and second floss posts 42 and 44, and a sliding engagement mechanism 46. The sliding engagement mechanism 46 is located on a bottom surface 47 opposite the thumb engagement surface 40 and is advantageously structured to be received by the channel 24 of FIG. 1. The first and second floss posts 42 and 44 protrude from a sloping surface 48 that connects the thumb engagement surface 40 to the bottom surface 47 and is situated on one side of the sliding member 26. FIGS. 5a and 5b, discussed further below, illustrates a novel floss post that may be employed as the first and second floss posts 42 and 44.

In operation, dental floss from the floss chamber 18 is attached to the second floss post 44 of the sliding member 26. The floss is then strung up to and through the aperture 30, through the aperture 32, along the length of the channel 24 and around the channel to the first floss post 42. The floss and the sliding member 26 thus create a closed loop. The floss is preferable pulled taut between the first and second floss posts 42 and 44 which provides a taut length of floss between the arms 20 and 22 at the distal end 14. The floss is strung within guiding structures of the shaft 12, discussed in more detail below in connection with FIG. 2. After the floss is connected as described above, linear movement of the sliding member 26 causes relative movement of the floss.

Once the dental floss is in place, the user places the distal end 14 of the shaft 12 within the mouth. The user places the length of floss between arms 20 and 22 at or near the base of a selected tooth to be cleaned. The user then wraps floss around the selected tooth by pushing or pulling the operative end, causing the flexible fork arms 20 and 22 to be pulled in by the floss which bends around the tooth. Once in place, the user may bite down upon the stabilizing member 34 to prevent excessive movement of the shaft 12. The user then begins applying reciprocating motion to the sliding member 26, preferably with his or her thumb. The reciprocating action causes the dental floss to reciprocate between arms 20 and 22, thereby effectuating cleaning of the nearby tooth or teeth. As the tooth is being cleaned, the user may rotated the shaft about the stabilizer bar 34, thereby raising or lowering the floss on the tooth or teeth being cleaned.

The stabilizing feature of the present invention helps increase control over the movement of the flossing device by preventing unwanted lateral and forward movement during flossing, while at the same time allowing for vertical movement. This feature offers greatly enhanced efficiency and convenience over prior art devices, and reduces stress on the user's hand and arm. Further, the use of a thumb-driven floss movement mechanism reduces complexity that could increase manufacturing costs and decrease liability.

Figure 4:
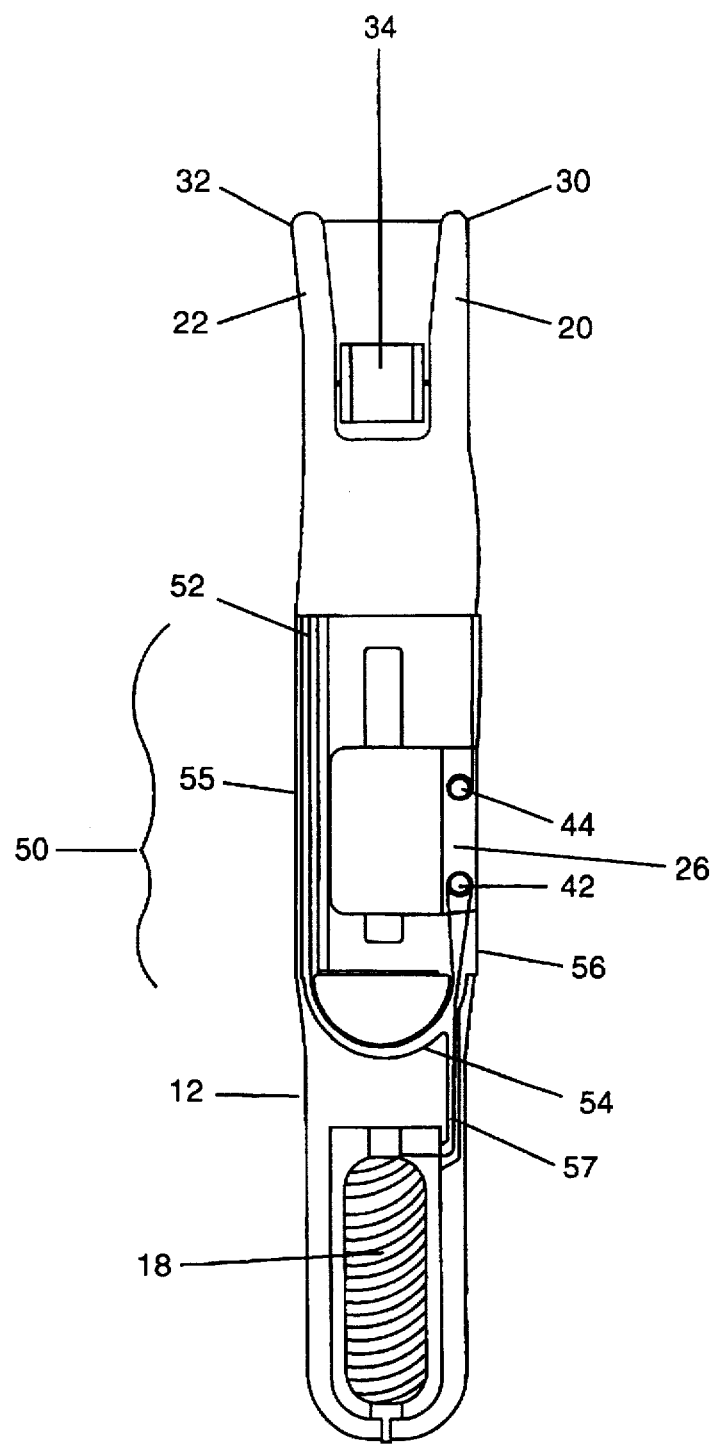
FIG. 4 shows a detailed top view of a flossing device similar to the flossing device shown in FIG. 1.

FIG. 4 shows a top view of a flossing device similar to the flossing device of FIG. 1, providing in further detail the interaction of dental floss with the shaft 12, sliding member 26 and arms 20 and 22. For ease of reference, the same reference numbers are used in FIG. 4 to identify corresponding parts from FIG. 1.

As can be seen from the top view in FIG. 4, the shaft 12 includes a middle section 50 defined generally by the length of travel of the sliding member 26, the middle section 50 having a far side 55 and a near side 56. The shaft 12 also includes a linear guide channel 52 located on the far side 55 of the middle section 50 and extending the length thereof, a semicircular guide channel 54 extending accurately from one end of the linear guide channel 52 to the near side 56 of the middle section 50, and a feed channel 57 extending generally from the floss chamber 18 to the near side 56 of the middle section 50.

Dental floss is generally strung through the feed channel 57 up to and around the first floss post 42, back through the near side 56 end of the semicircular guide channel 54, through the far side 55 end of the channel 54 and into the linear guide channel 52. The floss is then strung through the length of the linear guide channel 52, up to and through the second arm aperture 32, through the first arm aperture 30 and down along the first arm 20 to the second floss post 44. Preferably, the arms 20 and 22, as well as the portions of the shaft 12 that are between the arms 20 and 22 and the middle section 50 include a retaining means such as a channel for guiding the floss between the aperture 30 and the second floss post 44, and between the aperture 32 and the linear guide channel 52.

FIGS. 5a and 5b show a floss post 80 according to the present invention which is suitable for use in the flossing device 10. FIG. 5a illustrates a side-view cross section of the floss post 80 and FIG. 5b illustrates a top view of the floss post 80. The floss post 80 may suitably be used as the floss posts 42 and 44 of FIGS. 3 and 4.

In a preferred embodiment of the present invention, a floss post 80 comprises first and second retention pieces 81 and 82 respectively connected to the shaft or a device located on the shaft of a forked-shaped flosser. For example, the floss post 80 may be connected to the sloping surface 48 of the slidable mechanism 26 from FIG. 3 in a device similar to the flossing device 10. The first and second retention pieces 81 and 82 are respectively connected to the shaft 89 by first and second connection pieces 83 and 84. As shown in FIG. 5b, the first and second retention pieces 81 and 82 each have a substantially semicircular shape from the top view and are situated with respect to each other to form a circular structure bisected by a securing channel 85.

As shown in FIG. 5a, the first and second connection pieces 83 and 84 are generally smaller than the first and second half circular pieces and are of sufficient height to form a floss wrapping channel 86 between the shaft 89 and the first and second retention pieces 81 and 82. The first and second connection pieces 83 and 84 are spaced apart such that the space therebetween forms a portion of the securing channel 85. It is noted that as shown in FIG. 5a, the first and second retention pieces 81 and 82 each have a height or thickness which is sufficient to provide structural strength to retain any upward force executed by wrapped floss located within the floss wrapping channel 86.

In operation, to affix floss to a device such as the flossing device 10 of FIG. 1, the user wraps floss at least once around the first and second connection pieces 83 and 84 and within the floss retaining channel 86, and at least once through the securing channel 85. Wrapping the floss through both the floss retaining channel 86 and the securing channel 85 increases friction between the floss post 80 and the dental floss during flossing use, thereby reducing slippage. Prior art floss posts merely have a single floss retention channel similar to the floss retaining channel 86, around which floss is wrapped. In such prior designs, floss has a tendency to slip off the floss post and consequently release the tension required for effective flossing. In contrast, a flossing device according to the present invention with its dual channel design provides sufficient extra frictional force to reduce such slippage. Many if not all fork-shaped flossing devices which require the floss to be manually affixed would benefit from the use of the dual channel floss post 80 illustrated in FIGS. 5a and 5b.

The above described embodiment of the present invention is given by way of example only. Other implementations may be devised by those of ordinary skill in the art that incorporate the principles of the present invention and fall within the spirit and scope thereof.

What is claimed is:

1. A dental flossing device comprising a shaft having an operative end and a distal end, said distal end terminating in first and second fork arms, said fork arms each having a closed end connected to the shaft and an open end, said fork arms each having a closed end connected to the shaft and an open end, said fork arms each including an aperture for receiving dental floss and for guiding a length of dental floss between said first and second fork arms; and a stabilizing member rotatably attached to and between said first and second fork arms, said stabilizing member having a top tooth receiving surface and a bottom tooth receiving surface and operable to be engaged by teeth on both the top tooth receiving surface and the bottom tooth receiving surface to substantially prevent lateral and forward movement of the shaft during dental flossing.

2. The dental flossing device of claim 1 wherein said stabilizing member rotates around an axis generally defined by a line extending through said first and second fork arms.

3. The dental flossing device of claim 1 wherein said first and second arms taper away from one another such that the first fork arm is more distant from the second fork arm at the open end of the first and second fork arms than at the closed end of the first and second fork arms.

4. The dental flossing device of claim 3 further comprising a floss chamber for containing dental floss.

5. The dental flossing device of claim 1 further including a thumb-driven floss movement mechanism operably attached to the shaft and operable to cause dental floss to move between the apertures of the first and second fork arms.

6. The dental flossing device of claim 1 further comprising a sliding member slidably connected to a channel in the shaft, said sliding member having at least one means for connecting both ends of a length of dental floss such that sliding motion of the sliding member causes movement of the floss through the apertures in the first and second fork arms.

7. The dental flossing device of claim 6 wherein said sliding member further comprises at least one post for connecting both ends of length of dental floss.

8. The dental flossing device of claim 7 wherein said at least one post includes first and second channels for receiving and securing dental floss.

9. The dental flossing device of claim 1 wherein said stabilizing member further includes at least one retaining ridge.

10. A dental flossing device comprising a shaft having an operative end and a distal end, said distal end terminating in first and second fork arms, said fork arms each having a closed end connected to the shaft and an open end, said fork arms each including an aperture for receiving dental floss and for guiding a length of dental floss between said first and second fork arms;

an elongated linear channel located within said shaft; and a sliding member slidably connected to the elongated linear channel, said sliding member having at least one means for connecting both ends of a length of dental floss such that reciprocating sliding motion of the sliding member causes reciprocating movement of the dental floss through the apertures in the first and second fork arms.

11. The dental flossing device of claim 10 wherein said at least one means for connecting both ends of a length of dental floss includes at least one post.

12. The dental flossing device of claim 10 further comprising a floss chamber for containing dental floss.

13. The dental flossing device of claim 10 further comprising a stabilizing member attached to and between the first and second forks such that when said stabilizing member is engaged by teeth of a user, lateral and forward motion of the flossing device is inhibited.

14. The dental flossing device of claim 10 further comprising a stabilizing member rotatably attached to and between said first and second fork arms, said stabilizing member rotatable around an axis generally defined by a line extending through said first and second fork arms, said stabilizing member operable to be engaged by teeth to reduce movement of the shaft when the shaft is inserted into the mouth.

15. A dental flossing device comprising a shaft having an operative end and a distal end, said distal end terminating in first and second fork arms, said fork arms each having a closed end connected to the shaft and an open end, said fork arms each including an aperture for receiving dental floss and for guiding a length of dental floss between said first and second fork arms;

a stabilizing member rotatably attached to and between said first and second fork arms, said stabilizing member rotatable around an axis generally defined by a line extending through said first and second fork arms, said stabilizing member operable to be engaged by teeth to reduce movement of the shaft when the shaft is inserted into the mouth;

an elongated linear channel located within said shaft; and a sliding member slidably connected to the elongated linear channel, said sliding member having at least one means for connecting both ends of a length of dental floss such that reciprocating sliding motion of the sliding member causes reciprocating movement of the dental floss through the apertures in the first and second fork arms.

16. The dental flossing device of claim 15 further comprising a floss chamber located near the operative end of the shaft, said floss chamber for containing dental floss.

17. The dental flossing device of claim 15 wherein said first and second arms taper away from one another such that the first fork arm is more distant from the second fork arm at the open end of the first and second fork arms than at the closed end of the first and second fork arms.

18. The dental flossing device of claim 15 wherein said first and second arms are temporarily plastically deformable.

19. A dental flossing device comprising a shaft having an operative end and a distal end, said distal end terminating in first and second fork arms, said fork arms each having a closed end connected to the shaft and an open end, said fork arms each having a closed end connected to the shaft and an open end, said fork arms each including an aperture for receiving dental floss and for guiding a length of dental floss between said first and second fork arms;

a stabilizing member rotatably attached to and between said first and second fork arms, said stabilizing member having a top tooth receiving surface and a bottom tooth receiving surface and operable to be engaged by teeth on both the top tooth receiving surface and the bottom tooth receiving surface to substantially prevent lateral and forward movement of the shaft during dental flossing; and at least one floss post connected to the shaft.

* * * * *